United States Patent
Roy et al.

(10) Patent No.: US 6,682,490 B2
(45) Date of Patent: Jan. 27, 2004

(54) APPARATUS AND METHOD FOR MONITORING A CONDITION INSIDE A BODY CAVITY

(75) Inventors: Shuvo Roy, Cleveland, OH (US); Kenneth Ouriel, Pepper Pike, OH (US); Aaron J. Fleischman, University Heights, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 10/005,307

(22) Filed: Dec. 3, 2001

(65) Prior Publication Data

US 2003/0105388 A1 Jun. 5, 2003

(51) Int. Cl.$^7$ .......................... A61B 5/0215; A61B 5/07
(52) U.S. Cl. .................... 600/486; 600/302; 128/899
(58) Field of Search ................... 600/300, 301, 600/302, 485, 486, 561; 128/899, 903

(56) References Cited

U.S. PATENT DOCUMENTS

| | | | |
|---|---|---|---|
| 5,800,421 A | | 9/1998 | Lemelson |
| 5,935,084 A | * | 8/1999 | Southworth ................. 600/561 |
| 5,951,487 A | * | 9/1999 | Brehmeier-Flick et al. . 600/561 |
| 5,967,986 A | | 10/1999 | Cimochowski et al. |
| 6,025,725 A | | 2/2000 | Gershenfeld et al. |
| 6,111,520 A | | 8/2000 | Allen et al. |
| 6,159,156 A | | 12/2000 | Van Bockel |
| 6,206,835 B1 | | 3/2001 | Spillman, Jr. et al. |
| 6,268,161 B1 | | 7/2001 | Han et al. |
| 6,315,721 B2 | * | 11/2001 | Schulman et al. .......... 128/903 |

OTHER PUBLICATIONS

Santic, Ante. Biomedical Telemetry, Wiley Encyclopedia of Electrical and Electronics Engineering Online, J. Webster (ed.), Dec. 27, 1999.*

IEEE Transactions on Biomedical Engineering, vol. 47, No. 1, Jan. 2000 "A Portable. Microsystem–Bsed Telemetric Pressure and Temperature Measurement Unit", Bernd B. Flick and Reinhold Orglmeister.

* cited by examiner

Primary Examiner—Eric F. Winakur
Assistant Examiner—David J. McCrosky
(74) Attorney, Agent, or Firm—Tarolli, Sundheim, Covell & Tummino L.L.P.

(57) ABSTRACT

An apparatus (10) utilizes microelectricalmechanical systems (MEMS) technology to monitor a condition in a body cavity (28). The apparatus (10) comprises at least one sensor (42) for insertion into the body cavity. The sensor (42) generates a signal in response to a condition inside the body cavity (28). At least one telemetric device (44) is operatively coupled with the sensor (42). The telemetric device (44) is operable to receive the signal from the sensor (42) and to transmit an electromagnetic signal dependent upon the signal. The telemetric device (44) includes at least one coil member (82) extending from the telemetric device. The coil member (82) engages the body cavity (28) to secure the telemetric device (44) in the body cavity.

39 Claims, 5 Drawing Sheets

APPARATUS AND METHOD FOR MONITORING A CONDITION INSIDE A BODY CAVITY

TECHNICAL FIELD

The present invention is directed to an apparatus and method for monitoring a condition inside a body cavity.

BACKGROUND OF THE INVENTION

Information regarding the conditions inside a body cavity in a patient, such as a human, can be very helpful to a physician treating the patient. For example, it is desirable to monitor intercranial pressure to look for problems such as hemorrhaging and tumors. As another example, it is also desirable to monitor the pressure inside various blood vessels in the human body to help determine if a problem, such as stenosis or an aneurysm, exists.

In the case of an aneurysm, which is typically initially diagnosed using known imaging techniques, a variety of endoluminal grafts been developed to repair the aneurysm. An endoluminal graft can be introduced into a blood vessel through an open surgical procedure or through a minimally invasive, catheter-based delivery system. The endoluminal graft is placed in the blood vessel so that it isolates the aneurysm and provides a new lumen for the blood to flow through. Following placement of an endoluminal graft, it is desirable to monitor pressure between the aneurysm sac and the graft to look for endoleakage around the graft which could cause the blood vessel to rupture. Using conventional pressure measurement equipment, such pressure data is typically only able to be gathered during surgery.

Microelectromechanical systems, or MEMS, refers to a class of miniature electromechanical components and systems that are fabricated using techniques originally developed for fabricating microelectronics. MEMS devices, such as pressure sensors and strain gauges, manufactured using microfabrication and micromachining techniques can exhibit superior performance compared to their conventionally built counterparts, and are resistant to failure due to fatigue, corrosion, etc. Further, due to their extremely small size, MEMS devices can be utilized to perform functions in unique applications, such as the human body, that were not previously feasible using conventional devices.

SUMMARY OF THE INVENTION

The present invention is an apparatus for monitoring a condition in a body cavity. The apparatus comprises at least one sensor for insertion into a body cavity. The at least one sensor generates a signal in response to a condition inside the body cavity. At least one telemetric device is operatively coupled with the at least one sensor. The at least one telemetric device is operable to receive the signal from the at least one sensor and to transmit an electromagnetic (EMF) signal dependent upon the signal. The at least one telemetric device includes at least one coil member extending from the at least one telemetric device. The at least one coil member engages the body cavity to secure the at least one telemetric device in the body cavity.

According to one feature of the invention, the apparatus further comprises a compliant enclosure surrounding the at least one sensor and the at least one telemetric device.

According to another feature of the invention, the apparatus further comprises an external monitoring unit for receiving the EMF signal.

According to yet another feature of the invention, the apparatus further comprises an external power unit for inductively energizing the at least one telemetric device.

According to still another feature of the invention, the apparatus comprises a plurality of sensors and a corresponding plurality of telemetric devices that together form a sensor network.

In accordance with one embodiment of the invention, the at least one coil member comprises a plurality of coils extending in different directions.

In accordance with another embodiment of the invention, the at least one coil member is operatively coupled with the at least one telemetric device and functions as an antenna for transmitting the EMF signal.

The present invention additionally provides an apparatus for monitoring a condition in a body cavity. The apparatus comprises at least one sensor for insertion into a body cavity. The at least one sensor generates a signal in response to a condition inside the body cavity. At least one telemetric device is operatively coupled with the at least one sensor. The at least one telemetric device is operable to receive the signal from the at least one sensor and to transmit an electromagnetic (EMF) signal dependent upon the signal. The at least one telemetric device includes at least one coil member that is extendable inside the body cavity to minimize migration of the at least one telemetric device.

The present invention further provides an apparatus for monitoring pressure inside an aneurysm sac. The apparatus comprises at least one pressure sensor for insertion into the aneurysm sac. The at least one pressure sensor generates an output signal in response to and indicative of the pressure inside the aneurysm sac. At least one telemetric device is operatively coupled with the at least one pressure sensor. The at least one telemetric device is operable to receive the output signal from the at least one pressure sensor and to transmit an EMF signal dependent upon the output signal. The at least one telemetric device includes at least one coil member extending from the at least one telemetric device. The at least one coil member engages the aneurysm sac to secure the at least one telemetric device in the aneurysm sac.

The present invention also provides a method for monitoring a condition in an internal body cavity. A sensor is provided for generating an output signal in response to and indicative of a condition inside the body cavity. A telemetric device is provided for receiving the output signal from the sensor and transmitting an EMF signal dependent upon the output signal. The sensor and the telemetric device are encapsulated in a compliant enclosure to form a transducer assembly. At least one coil member is connected with the transducer assembly. The at least one coil member projects from the compliant enclosure. The transducer assembly is inserted into a body cavity. The transducer assembly is attached to the body cavity with the at least one coil member. The EMF signal from the sensor is then monitored and transmitted by the telemetric device.

The present invention further provides a method for monitoring a condition in an internal body cavity. A sensor is provided for generating an output signal in response to and indicative of a condition inside the body cavity. A telemetric device is provided for receiving the output signal from the sensor and transmitting an EMF signal dependent upon the output signal. The sensor and the telemetric device are encapsulated in a compliant enclosure to form a transducer assembly. At least one coil member is connected with the transducer assembly. The at least one coil member is extendable from the compliant enclosure inside a body cavity. The transducer assembly is inserted into a body cavity. The at least one coil member is extended inside the body cavity to minimize migration of the transducer assembly in the body cavity. The EMF signal from the sensor is then monitored and transmitted by the telemetric device.

BRIEF DESCRIPTION OF THE DRAWINGS

The foregoing and other features of the present invention will become apparent to those skilled in the art to which the present invention relates upon reading the following description with reference to the accompanying drawings, in which.

DESCRIPTION OF EMBODIMENTS

Figure 1:
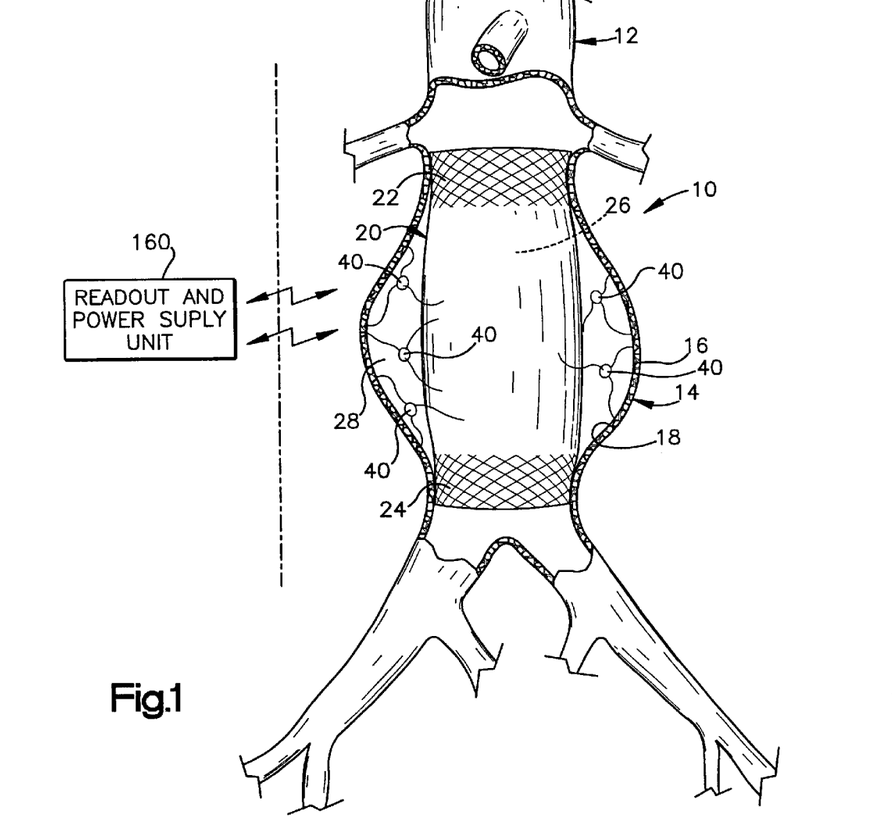
FIG. 1 is a front view, partly in section, of a body cavity and illustrates an apparatus for monitoring a condition in the body cavity.

The present invention is directed to an apparatus and method for monitoring a condition inside a body cavity. As representative of the present invention, FIG. 1 illustrates an apparatus 10 for monitoring pressure in an aorta 12. The aorta 12 has an aneurysm 14 that forms an aneurysmal sac 16 in the aorta. The aneurysm 14 has been treated by inserting an endoluminal graft 20 into the aneurysmal sac 16 as is known in the art. As is described further below, the apparatus 10 monitors pressure inside the aneurysmal sac 16 to look for endoleakage around the graft 20 which could cause the aneurysmal sac to rupture. It should be understood that the apparatus 10 could be used to monitor pressure in a wide variety of other cavities or areas of a body.

The graft 20 has a known configuration and is expandable to engage an inner surface 18 of the aorta 12. An upper (as viewed in the Figures) end 22 of the graft 20 engages the inner surface 18 of the aorta 12 above the aneurysm 14, while a lower (as viewed in the Figures) end 24 of the graft engages the inner surface of the aorta below the aneurysm. The upper and lower ends 22 and 24 of the graft 20 may include hooks or barbs (not shown) for attaching the graft to the aorta 12. The engagement and attachment of the upper and lower ends 22 and 24 of the graft 20 to the aorta 12 is intended to seal off the aneurysmal sac 16 from blood flow that could cause the aneurysm 14 to rupture, and to instead direct the blood flow through a conduit 26 formed by the graft.

Figure 2:
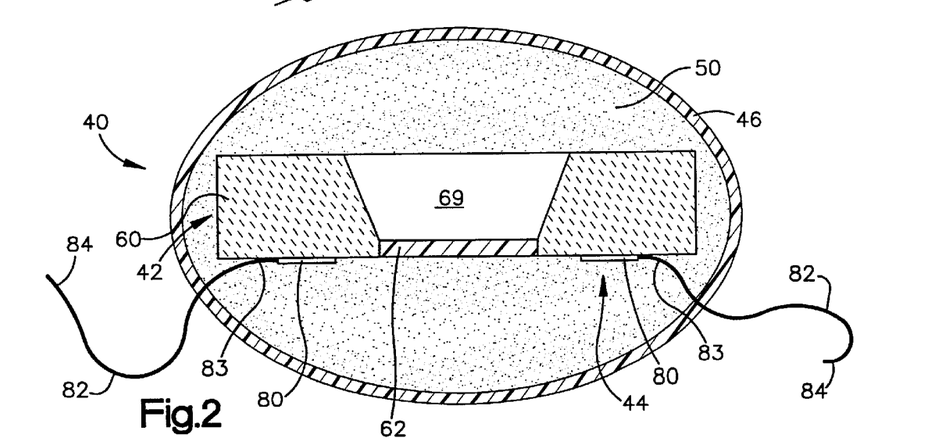
FIG. 2 is an enlarged sectional view of a component of the apparatus.

After the graft 20 has been positioned in the aneurysmal sac 16 and secured to the aorta 12 as shown in FIG. 1, the apparatus 10 is deployed to monitor the blood pressure in a cavity 28 defined between the aneurysmal sac 16 and the graft 20. It should be understood, however, that the apparatus 10 could be deployed prior to the placement of the graft 20 in the aorta 12. The apparatus 10 comprises at least one miniature transducer assembly 40. As shown in FIG. 2, the transducer assembly 40 comprises a pressure sensor 42 and a telemetric device 44. The transducer assembly 40 is encased in a compliant enclosure 46 that is responsive to external pressure. The compliant enclosure 46 is a balloon-like sac made of a biocompatible material that surrounds the transducer assembly 40. Alternatively, the compliant enclosure 46 may comprise a gel, gelatin, or film of biocompatible materials as is discussed further below.

The compliant enclosure 46 is filled with a liquid (or a gel) 50, such as silicone, saline, or other suitable material, that is biocompatible. The properties of the liquid 50 allow it to transmit pressure exerted against the compliant enclosure 46 uniformly against the sensing element (discussed below) of the pressure sensor 42, while isolating the electrical components and circuitry of the transducer assembly 40 from any corrosive media.

The illustrated pressure sensor 42 is of a known configuration and is made using known micromachining processes, microfabrication processes, or other suitable MEMS fabrication techniques. Pressure sensors of this type are commercially available from Motorola, Inc. of Schaumburg, Ill. and TRW Novasensor of Fremont, Calif. It should be understood that any pressure sensor that meets the biocompatibility and size requirements may be used.

Figure 3:
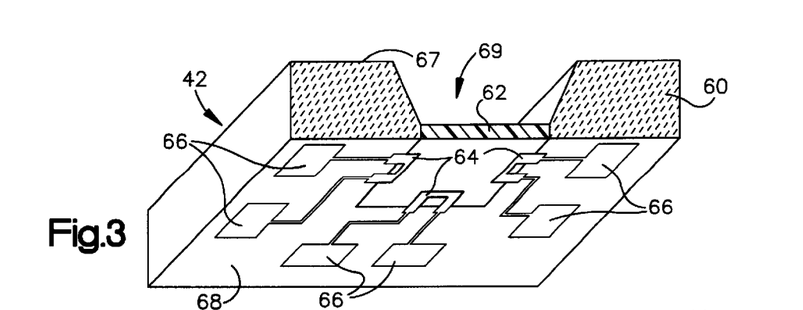
FIG. 3 is a perspective view of a portion of the component shown in FIG. 2.

The illustrated pressure sensor 42 is a piezoresistive device, but it should be understood that other types of pressure sensors, such as a piezoelectric and capacitive sensors, could be substituted. As best seen in FIG. 3, the pressure sensor 42 comprises a substrate 60, a sensing diaphragm 62, a plurality of patterned resistors 64, and a plurality of bond pads 66, two of which are associated with each of the resistors.

The substrate 60 has upper and lower surfaces 67 and 68, respectively, and is made of silicon, but could alternatively be made of another suitable material. The substrate 60 has a well region 69 that extends between the upper and lower surfaces 67 and 68 and that is formed using a conventional microfabrication and bulk micromachining processes including lithography and etching. The sensing diaphragm 62, which extends across the well region 69, is also made of silicon and is defined by the lithography and etching processes. The resistors 64 and the bond pads 66 are formed from a metal or polysilicon layer that is deposited, patterned, and etched in a known manner on the lower surface 68 of the substrate 60. The resistors 64 could also be formed by doping the silicon using boron, phosphorus, arsenic, or another suitable material to render a region of the silicon with an appropriate conductivity and polarity to create junction-isolated piezoresistors. As will be apparent to those skilled in the art, other methods, such as SIMOX, wafer bonding, and dissolved wafer approaches, could also be used. The resistors 64 are positioned along the edges of the sensing diaphragm 62 to detect strain in the sensing diaphragm caused by pressure differentials. The resistors 64 could alternatively be positioned in another region of high or maximum strain in the sensing diaphragm 62.

Figure 4:
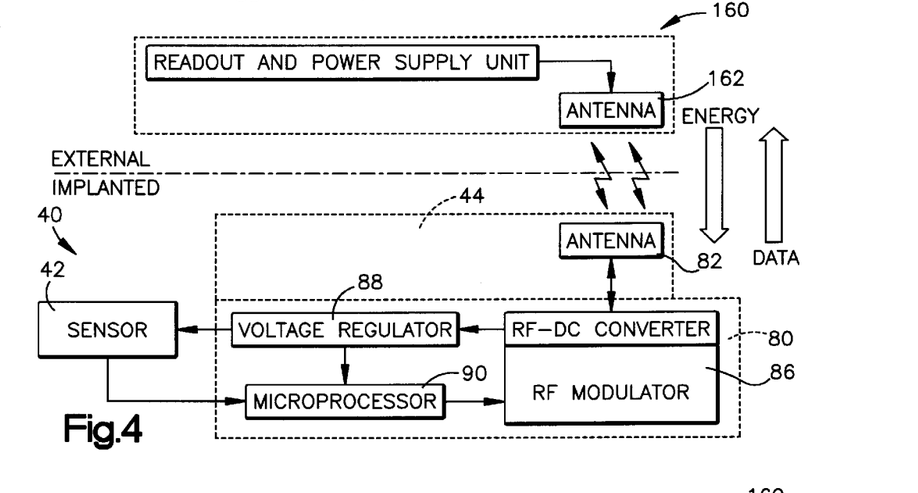
FIG. 4 is a schematic block diagram of the apparatus for monitoring a condition in the body cavity.

The telemetric device 44 in the transducer assembly 40 includes an electronics module 80 (FIG. 2) and a plurality of coil members 82. The electronics module 80 is operatively coupled to the pressure sensor 42 by the bond pads 66 in a manner not shown. As shown in the block diagram of FIG. 4, the electronics module 80 comprises integrated circuitry. The integrated circuitry includes an RF-DC converter/modulator 86 and a voltage regulator 88 operatively coupled between the antenna 82 and the pressure sensor 42. The integrated circuitry further includes a microprocessor 90 operatively coupled between the pressure sensor 42 and the RF-DC converter/modulator 86. To protect the circuitry of the electronics module 80, the electronics module may be coated with a soft polymeric film, such as parylene or polydimethylsiloxane (PDMS), or a biocompatible epoxy.

The telemetric device 44 in the transducer assembly 40 includes an electronics module 80 (FIG. 2) and a plurality of coil members 82. The electronics module 80 is operatively coupled to the pressure sensor 42 by the bond pads 66 in a manner not shown. As shown in the block diagram of FIG. 4, the electronics module 80 comprises integrated circuitry. The integrated circuitry includes an RF-DC converter/modulator 84 and a voltage regulator 86 operatively coupled between the antenna 82 and the pressure sensor 42. The integrated circuitry further includes a microprocessor 88 operatively coupled between the pressure sensor 42 and the RF-DC converter/modulator 84. To protect the circuitry of the electronics module 80, the electronics module may be coated with a soft polymeric film, such as parylene or polydimethylsiloxane (PDMS), or a biocompatible epoxy.

Two or more coil members 82 extend from the telemetric device 44 in the transducer assembly 40. The coil members 82 function as antennas and are operatively (electrically) coupled at a proximal end 83 with the electronics module 80 in a manner not shown. A distal end 84 of each of the coil members 82 is used to anchor the transducer assembly 40 to a surface as described further below. The coil members 82 project in different directions through the compliant enclosure 46, which seals itself around the coil members. The coil members 82 are made from a nickel titanium alloy, commonly referred to as Nitinol, which has known shape memory properties. The coil members 82 may alternatively be made from another biocompatible shape memory alloy, or from another material suitable for an antenna.

As is known in the art, shape memory alloys have the ability to return to a predetermined shape when heated. When a shape memory alloy is cold, or below its transition temperature range (TTR), the material has a low yield strength and can be deformed into a new shape, which it will retain until heated. However, when a shape memory alloy is heated above its TTR, the material undergoes a change in crystal structure (from a martensite structure to an austenite structure), which causes the material to return to its original, or "memorized" shape. A memorized shape is imprinted into a shape memory alloy by first holding the material in the desired shape at a high temperature, and then continuing to hold the material in the desired shape as it cools through its TTR.

The apparatus 10 further includes an external (meaning it is located outside of and/or remote from the patient's body) readout/power supply unit 160 (FIG. 4) having an integrated antenna 162. The readout/power supply unit 160 contains circuitry known in the art and therefore not described in any detail.

The readout/power supply unit 160 may be a hand-held device or a larger piece of equipment found at a physician's office. The readout/power supply unit 160 could also be a device worn by the patient.

Figure 5:
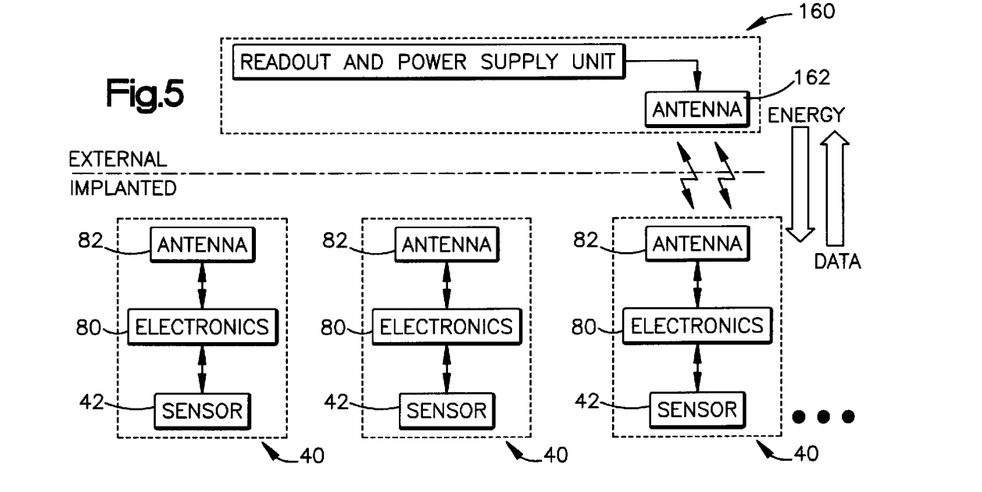
FIG. 5 is another schematic block diagram of the apparatus for monitoring a condition in the body cavity.

The readout/power supply unit 160 is operable to transmit electrical energy as well as receive, display, and store data through the antenna 162 as described further below. Further, the readout/power supply unit 160 is able to transmit electrical energy and exchange data simultaneously with several transducer assemblies 40, as is illustrated in FIG. 5.

Once the endoluminal graft 20 has been placed into the aneurysmal sac 16 as shown in FIG. 1, the apparatus 10 can be used to monitor pressure inside the aneurysmal sac 16 to look for endoleakage around the graft 20 and into the cavity 28 which could cause the aneurysmal sac to rupture. Such endoleakage will be evident by a pressure increase inside the cavity 28.

As may be seen in FIG. 1, several of the transducer assemblies 40 are inserted into the cavity 28 between the graft 20 and the aneurysmal sac 16. It should be understood that the exact quantity of transducer assemblies 40 inserted into a given body cavity will be selected based on the particular application of the present invention. Due to their size, the transducer assemblies 40 can be delivered sequentially through a single needle or catheter (not shown) inserted through the wall of the aneurysm 14. Alternatively, the transducer assemblies 40 could be inserted into the cavity 28 using an intervascular surgical technique, or could be mounted on the outside of the graft 20.

Immediately prior to insertion of the transducer assemblies 40 into the cavity 28, the transducer assemblies may undergo a cooling process which causes the coil members 82 to coil up (not shown) and thus compress in overall size, which may aid in delivery. Upon being inserted into the cavity 28, the transducer assemblies 40 are exposed to the warmer environment of the human body, causing the coil members 82 to expand and return to their memorized shape shown in FIGS. 1 and 2.

Upon insertion into the cavity 28, the transducer assemblies 40 deploy into various locations throughout the cavity 28. Inside the cavity 28, the coil members 82 associated with each of the transducer assemblies 40 expand to reduce or prevent migration of the transducer assemblies in the aneurysmal sac 16. The expanded coil members 82 minimize migration of the transducer assemblies 40 by providing increased drag, and also serve as a means for spacing the transducer assemblies apart. By virtue of the expanded coil members 82, the transducer assemblies 40 can attach themselves to the inner surface 18 of the aorta 12 in the aneurysmal sac 16. The transducer assemblies 40 attach to the inner surface 18 of the aorta 12 by the distal end 84 of one or more of the coil members 82 on each transducer assembly catching or snagging on the inner surface of the aorta. It is contemplated that the distal end 84 of one of the coil members 82 could also catch or snag on the outer surface of the graft 20 to further secure the transducer assembly. The dispersed pattern of transducer assemblies 40, such as is shown in FIG. 1, forms a sensor network for mapping the pressure distribution inside the cavity 28.

To begin monitoring the pressure inside the cavity 28, the readout/power supply-unit 160 transmits electrical energy in the form of an electromagnetic field (EMF) signal, or more specifically a radio frequency (RF) signal, through the antenna 162 to each of the transducer assemblies 40 in the cavity. The RF signal is received through the coil members 82 on each of the transducer assemblies 40 and is converted into a DC signal to inductively energize the circuitry in the pressure sensors 42.

Each of the pressure sensors 42 in the cavity 28 detects changes in electrical resistance caused by deformation and strain on the sensing diaphragm 62. The changes in resistance detected by each of the pressure sensors 42 correspond to applied pressure and a data signal dependent upon the sensed condition is generated by the electronics module 80. The data signal is then transmitted, in a wireless fashion, from the coil members 82 on each of the transducer assemblies 40 to the antenna 162 in the readout/power supply unit 160. The data signals transmitted are pulse-width-modulated (PWM) signals that have RF carrier frequencies. It should be understood that other signal types (e.g., frequency modulation (FM) or frequency shift key (FSK)) could also be used. Each transducer assembly 40 operates within a specific and distinct carrier frequency band so that each transducer assembly can be identified.

The antenna 162 in the readout/power supply unit 160 receives the data signals from the transducer assemblies 40, processes the data signals, and displays pressure data based on the data signals that correspond to the pressure sensed by each of the pressure sensors 42. The pressure data may be displayed in any number of formats, such as absolute values or plots. The pressure data may also be stored by the readout/power supply unit 160.

The data received by the readout/power supply unit 160 provides an in vivo assessment of the pressure inside the cavity 28. Further, by placing multiple transducer assemblies 40 into the cavity 28, the apparatus 10 can monitor the distribution of pressure inside the cavity, which can provide useful information about the location of an endoleak or other anomaly such as a particularly weakened area of the aneurysm 14. The apparatus 10 described above provides the ability to continuously, or on-demand, monitor the pressure inside the cavity 28 during the post-operative period. Because of this ability to continuously or on-demand monitor the pressure inside the cavity 28, it may be possible to appropriately time, or even avoid, additional surgery. Further, information gathered from such in vivo assessments can lead to improvements in surgical techniques and graft design.

Figure 6:
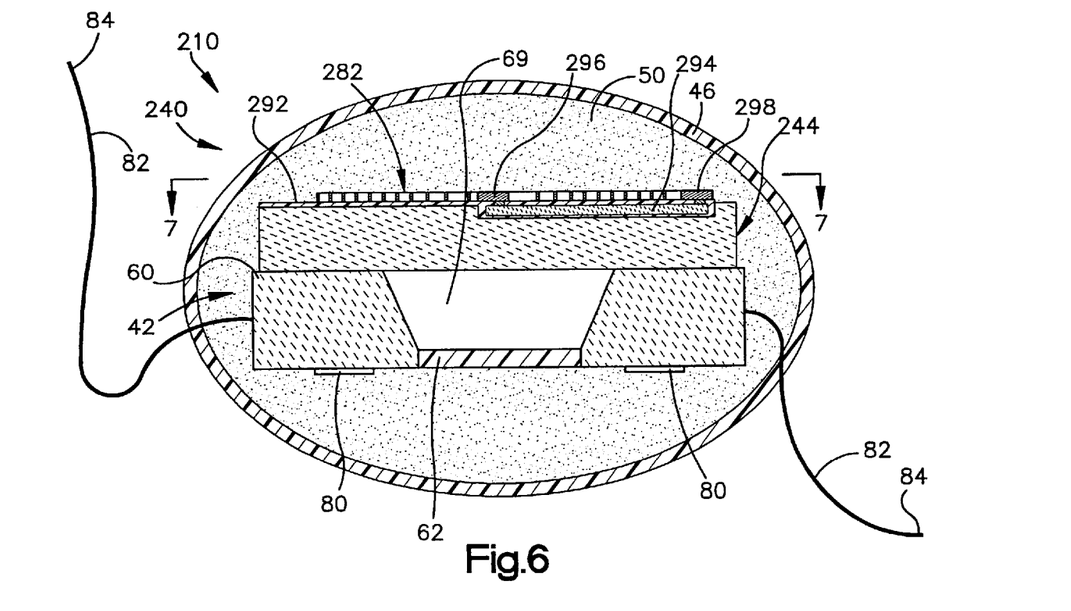
FIG. 6 is a sectional view similar to FIG. 2 illustrating a second embodiment.
Figure 7:
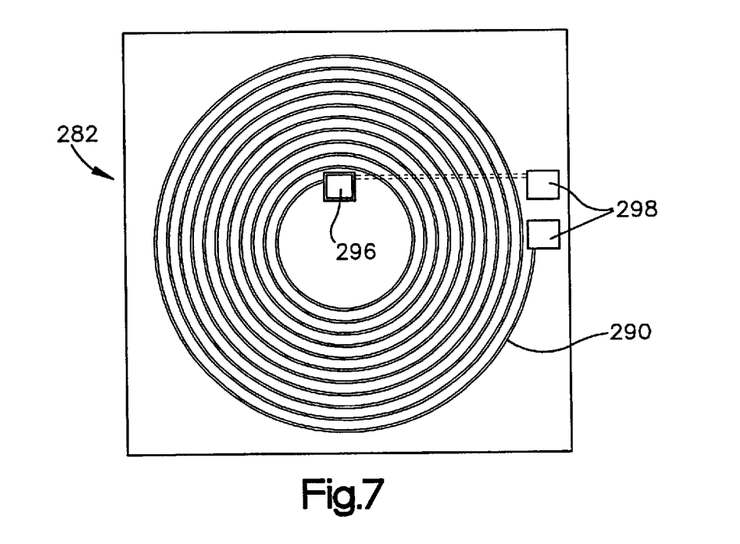
FIG. 7 is a plan view taken along line 7—7 in FIG. 6.

FIGS. 6 and 7 illustrate an apparatus 210 for monitoring pressure inside the body cavity 28 constructed in accordance with a second embodiment of the present invention. In the second embodiment of FIGS. 6 and 7, reference numbers that are the same as those used in the first embodiment of FIGS. 1–5 designate components that are the same as components in the first embodiment.

According to the second embodiment of FIGS. 6 and 7, the apparatus 210 utilizes a transducer assembly 240 that is slightly different from the transducer assembly 40. The transducer assembly 240 is surrounded by the compliant enclosure 46, which filled with the liquid (or gel) 50. The transducer assembly 240 comprises the pressure sensor 42 and a telemetric device 244. The telemetric device 244 includes the electronics module 80 and an antenna 282.

The antenna 282 may be fabricated on the substrate of the pressure sensor 42 using known micromachining or microfabrication techniques, or may alternatively be fabricated separately and joined with the pressure sensor. The antenna 282 comprises a spiral-shaped coil 290 of metal deposited over an oxide layer 292 (FIG. 6). A layer of doped polysilicon 294 underneath the oxide layer 292 establishes an electrical connection between a contact 296 in the center of the coil 290 and one of two contacts 298 outside the coil. The contacts 298 of the antenna 282 outside of the coil 290 are operatively coupled with the electronics module 80 in a manner not shown. For protection purposes, the antenna 282 may be coated with a soft polymeric film, such as parylene or PDMS, or a biocompatible epoxy.

Two or more coil members 82 extend from the transducer assembly 240. Unlike the first embodiment of FIGS. 1–5, the coil members 82 are not electrically coupled with the electronics module 80. Rather, the coil members 82 are attached, by a known method such as soldering, ultrasonic bonding, or laser welding, to the pressure transducer 42, and are simply used to anchor the transducer assembly 240 to a surface inside the cavity 28 as described above. The coil members 82 project in different directions through the compliant enclosure 46, which seals itself around the coil members. As in the previous embodiment, the coil members 82 are made from a nickel titanium alloy, commonly referred to as Nitinol, which has known shape memory properties, but could alternatively be made from another biocompatible material.

Once the endoluminal graft 20 has been placed into the aneurysmal sac 16 as shown in FIG. 1, the apparatus 210 can be used to monitor pressure inside the aneurysmal sac 16 to look for endoleakage into the cavity 28 in the same manner as described in the first embodiment of FIGS. 1–5. A plurality of the transducer assemblies 240 are inserted into the cavity 28 between the graft 20 and the aneurysmal sac 16. Immediately prior to insertion of the transducer assemblies 240 into the cavity 28, the transducer assemblies may undergo a cooling process which causes the coil members 82 to compress in overall size.

Upon being inserted into the warmer environment of the cavity 28, the coil members 82 expand and return to their memorized shape shown in FIG. 6. After insertion into the cavity 28, the transducer assemblies 240 deploy into various locations throughout the cavity and become attached to the inner surface 18 of the aorta 12. The transducer assemblies 240 are attached to the inner surface 18 of the aorta 12 by the distal end 84 of one or more of the coil members 82 on each transducer assembly 240 catching or snagging on the inner surface of the aorta. The deployed pattern of transducer assemblies 240, such as is shown in FIG. 1, forms a sensor network for mapping the pressure distribution inside the cavity 28.

The pressure inside the cavity 28 is then monitored using the apparatus 210 in the same manner as described above with regard to the first embodiment. The readout/power supply unit 160 transmits electrical energy in the form of an electromagnetic field (EMF) signal, or more specifically a radio frequency (RF) signal, through the antenna 162 to each of the transducer assemblies 240 in the cavity 28. The RF signal is received through the antenna 282 on each of the transducer assemblies 240 and is converted into a DC signal to inductively energize the circuitry in the pressure sensors 42.

Each of the pressure sensors 42 in the cavity 28 detects changes in electrical resistance caused by deformation and strain on the sensing diaphragm 62. The changes in resistance detected by each of the pressure sensors 42 correspond to applied pressure and a data signal dependent upon the sensed condition is generated by the electronics module 80. The data signal is then transmitted percutaneously from the antenna 282 on each of the transducer assemblies 240 to the antenna 162 in the readout/power supply unit 160. The data signals transmitted are pulse-width-modulated (PWM) signals that have RF carrier frequencies. It should be understood that other signal types (e.g., frequency modulation (FM) or frequency shift key (FSK)) could also be used. Each transducer assembly 240 operates within a specific and distinct carrier frequency band so that each transducer assembly can be identified.

The antenna 162 in the readout/power supply unit 160 receives the data signals from the transducer assemblies 240, processes the data signals, and displays pressure data based on the data signals that correspond to the pressure sensed by each of the pressure sensors 42. The pressure data may be displayed in any number of formats, such as absolute values or plots. The pressure data may also be stored by the readout/power supply unit 160.

The data received by the readout/power supply unit 160 provides an in vivo assessment of the pressure inside the cavity. Further, by placing multiple transducer assemblies 240 into the cavity 28, the apparatus 210 can monitor the distribution of pressure inside the cavity, which can provide useful information about the location of an endoleak or other anomaly such as a particularly weakened area of the aneurysm 14. The apparatus 210 described above provides the ability to continuously, or on-demand, monitor the pressure inside the cavity during the post-operative period.

Figure 8:
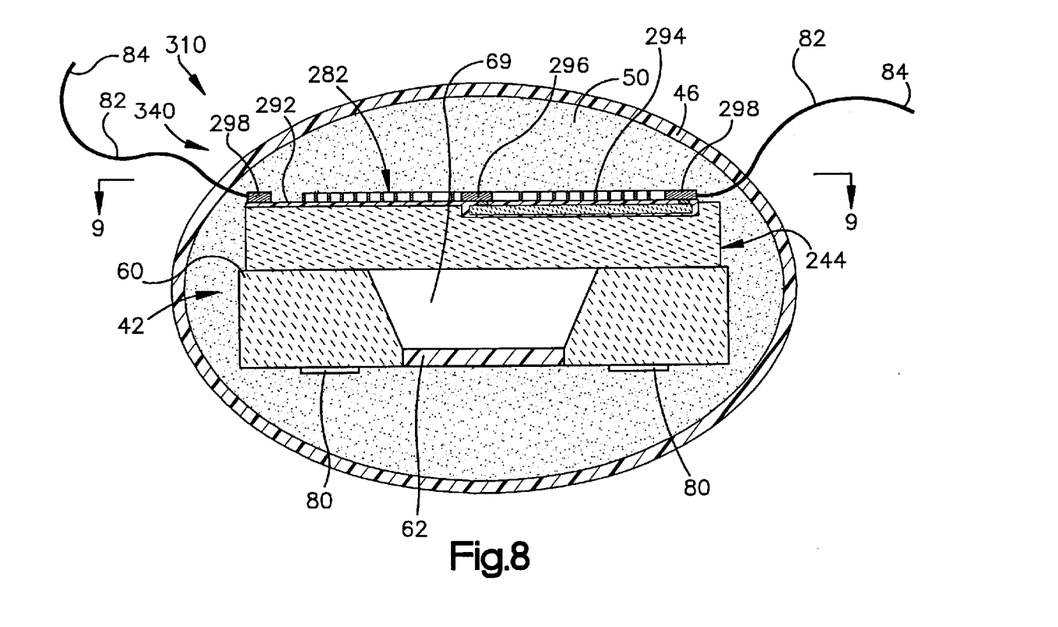
FIG. 8 is a sectional view similar to FIG. 2 illustrating a third embodiment.
Figure 9:
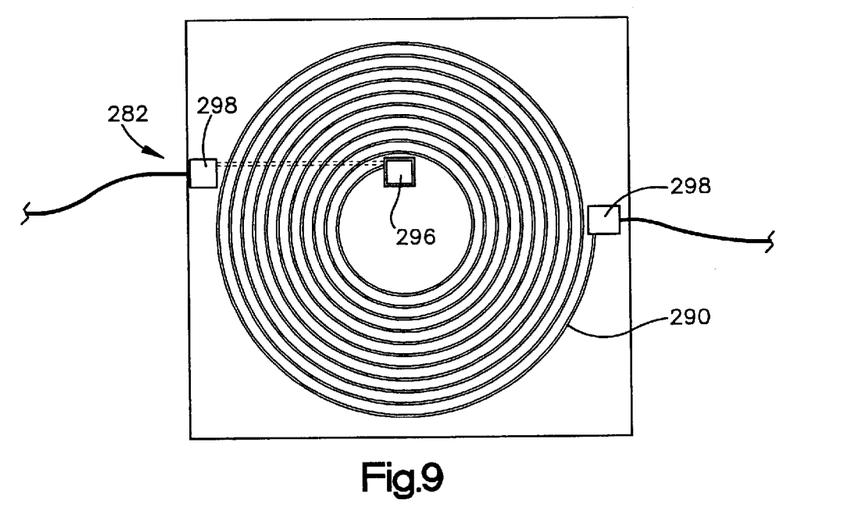
FIG. 9 is a plan view taken along line 9—9 in FIG. 8.

FIGS. 8 and 9 illustrate an apparatus 310 for monitoring pressure inside the body cavity 28 constructed in accordance with a third embodiment of the present invention. In the third embodiment of FIGS. 8 and 9, reference numbers that are the same as those used in the previous embodiments designate components that are the same as components in the previous embodiments.

According to the third embodiment of FIGS. 8 and 9, the apparatus 310 utilizes another different transducer assembly 340. The transducer assembly 340 includes the pressure sensor 42 and the telemetric device 244 having the antenna 282 described above. Two or more coil members 82 extend from the antenna 282 in the transducer assembly 340 and are electrically coupled with the antenna. The coil members 82 are used to anchor the transducer assembly 240 to a surface inside the body cavity 28 as described above, but also function as extensions of the antenna 282 to improve the exchange of electrical signals between the transducer assembly 340 and the readout/power supply unit 160. As in the previous embodiments, the coil members 82 are made from a nickel titanium alloy, commonly referred to as Nitinol, which has known shape memory properties, but could alternatively be made from another biocompatible material.

The apparatus 310 according to the third embodiment is used in the same manner as described above with regard to the first embodiment to monitor pressure inside the cavity 28. The data received by the readout/power supply unit 160 provides an in vivo assessment of the pressure inside the cavity 28. Further, by placing multiple transducer assemblies 340 into the cavity 28, the apparatus 310 can monitor the distribution of pressure inside the cavity, which can provide useful information about the location of an endoleak or other anomaly such as a particularly weakened area of the aneurysm 14. The apparatus 310 described above provides the ability to continuously, or on-demand, monitor the pressure inside the cavity 28 during the post-operative period.

Figure 10:
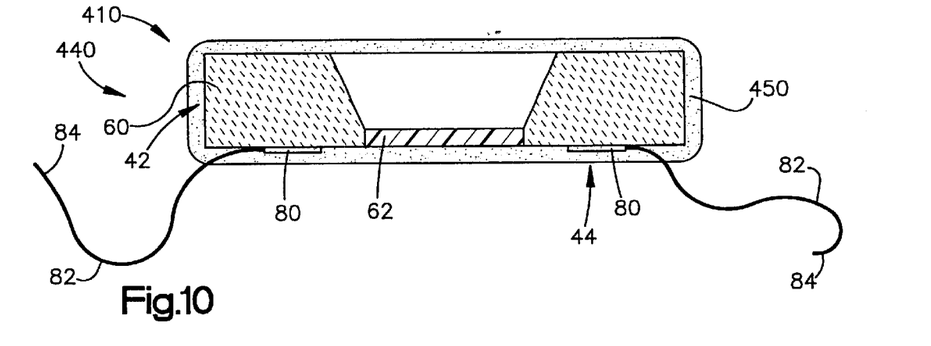
FIG. 10 is a sectional view similar to FIG. 2 illustrating a fourth embodiment.

FIG. 10 illustrates an apparatus 410 for monitoring pressure inside the body cavity 28 constructed in accordance with a fourth embodiment of the present invention. In the fourth embodiment of FIG. 10, reference numbers that are the same as those used in the previous embodiments designate components that are the same as components in the previous embodiments.

According to the fourth embodiment, the apparatus 410 comprises a transducer assembly 440 that is similar to the transducer assembly 40 of FIG. 2, but does not include the compliant enclosure 46 filled with the liquid 50. Instead, the pressure sensor 42 and telemetric device 44 are packaged within a biomolecular coating 450. Exposing the transducer assembly 440 to solutions containing desired biomolecules, leads to monolayer coating of the outer surfaces of the transducer assembly. The desired biomolecules may be collagen, hyaluronan, glycol, polyurethane, or other suitable biomolecular material. Alternatively, a film of biomolecules could cover the transducer assembly 440. Further, thin layers of another suitable biocompatible material, such as parylene or PDMS, could instead be applied to the outer surfaces of the transducer assembly 440.

The apparatus 410 according to the fourth embodiment is used in the same manner as described above with regard to the first embodiment to monitor pressure inside the cavity 28. The data received by the readout/power supply unit 160 provides an in vivo assessment of the pressure inside the cavity 28. Further, by placing multiple transducer assemblies 440 into the cavity 28, the apparatus 410 can monitor the distribution of pressure inside the cavity, which can provide useful information about the location of an endoleak or other anomaly such as a particularly weakened area of the aneurysm 14. The apparatus 410 described above provides the ability to continuously, or on-demand, monitor the pressure inside the cavity 28 during the post-operative period.

Figure 11:
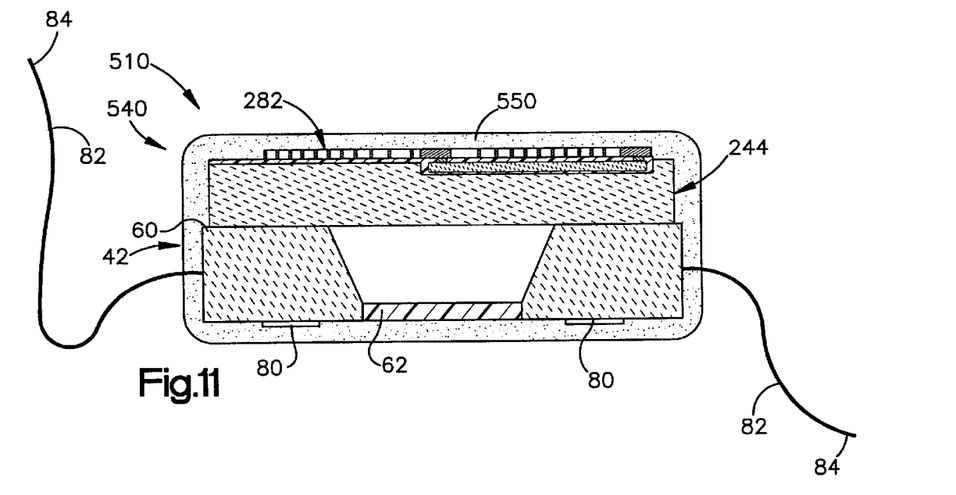
FIG. 11 is a sectional view similar to FIG. 6 illustrating a fifth embodiment.

FIG. 11 illustrates an apparatus 510 for monitoring pressure inside the body cavity 28 constructed in accordance with a fifth embodiment of the present invention. In the fifth embodiment of FIG. 11, reference numbers that are the same as those used in the previous embodiments designate components that are the same as components in the previous embodiments.

According to the fifth embodiment, the apparatus 510 comprises a transducer assembly 540 that is similar to the transducer assembly 240 of FIG. 6, but does not include the compliant enclosure 46 filled with the liquid 50. Instead, the pressure sensor 42 and telemetric device 244 are packaged within a biomolecular coating 550. Exposing the transducer assembly 540 to solutions containing desired biomolecules, leads to monolayer coating of the outer surfaces of the transducer assembly. The desired biomolecules may be collagen, hyaluronan, glycol, polyurethane, or other suitable biomolecular material. Alternatively, a film of biomolecules could cover the transducer assembly 540. Further, thin layers of another suitable biocompatible material, such as parylene or PDMS, could instead be applied to the outer surfaces of the transducer assembly 540.

The apparatus 510 according to the fifth embodiment is used in the same manner as described above with regard to the first embodiment to monitor pressure inside the cavity 28. The data received by the readout/power supply unit 160 provides an in vivo assessment of the pressure inside the cavity 28. Further, by placing multiple transducer assemblies 540 into the cavity 28, the apparatus 510 can monitor the distribution of pressure inside the cavity, which can provide useful information about the location of an endoleak or other anomaly such as a particularly weakened area of the aneurysm 14. The apparatus 510 described above provides the ability to continuously, or on-demand, monitor the pressure inside the cavity 28 during the post-operative period.

Figure 12:
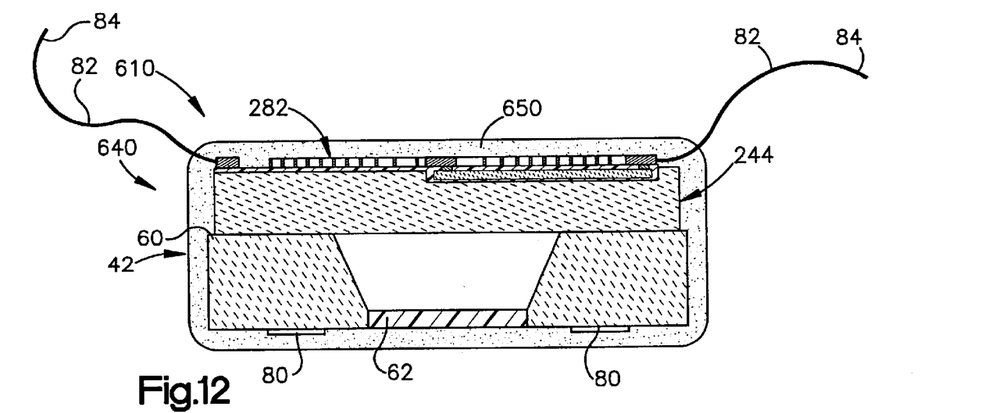
FIG. 12 is a sectional view similar to FIG. 8 illustrating a sixth embodiment.

FIG. 12 illustrates an apparatus 610 for monitoring pressure inside the body cavity 28 constructed in accordance with a sixth embodiment of the present invention. In the sixth embodiment of FIG. 12, reference numbers that are the same as those used in the previous embodiments designate components that are the same as components in the previous embodiments.

According to the sixth embodiment, the apparatus 610 comprises a transducer assembly 640 that is similar to the transducer assembly 340 of FIG. 8, but does not include the compliant enclosure 46 filled with the liquid 50. Instead, the pressure sensor 42 and telemetric device 244 are packaged within a biomolecular coating 650. Exposing the transducer assembly 640 to solutions containing desired biomolecules, leads to monolayer coating of the outer surfaces of the transducer assembly 640. The desired biomolecules may be collagen, hyaluronan, glycol, polyurethane, or other suitable biomolecular material. Alternatively, a film of biomolecules could cover the transducer assembly 640. Further, thin layers of another suitable biocompatible material, such as parylene or PDMS, could instead be applied to the outer surfaces of the transducer assembly 640.

The apparatus 610 according to the sixth embodiment is used in the same manner as described above with regard to the first embodiment to monitor pressure inside the cavity 28. The data received by the readout/power supply unit 160 provides an in vivo assessment of the pressure inside the cavity 28. Further, by placing multiple transducer assemblies 640 into the cavity 28, the apparatus 610 can monitor the distribution of pressure inside the cavity, which can provide useful information about the location of an endoleak or other anomaly such as a particularly weakened area of the aneurysm 14. The apparatus 610 described above provides the ability to continuously, or on-demand, monitor the pressure inside the cavity 28 during the post-operative period.

In addition to the telemetry scheme described above, it is contemplated that an alternative telemetry scheme using a tank circuit (not shown) could be employed using a capacitive-type sensor in each of the aforementioned embodiments of the present invention. It is known that a change in capacitance or inductance on a sensor, such as a pressure sensor or a strain gauge, can be detected using a tank circuit. Such a tank circuit has either a variable capacitance and a fixed inductance, or a variable inductance and a fixed capacitance.

If the tank circuit has a variable capacitance, the capacitance will change as the pressure or strain, depending on the type of sensor, changes. This change in capacitance leads to changes in resonant frequency that can be detected. The capacitance changes can then be calculated using the following equation:

$$f_0 = 1/2\pi(LC)^{1/2},$$

where L is the inductance and C is the capacitance. This same equation is also used to calculate inductance changes if the capacitance of the tank circuit is fixed. In the embodiments discussed above where there are multiple sensors, each sensor is designed to operate within a specific resonant frequency band. The tank circuit is then swept over range of frequencies so that the individual resonant frequency of each sensor, which corresponds to the output of each sensor, can be identified.

In the present invention, the tank circuit telemetry scheme could be employed in several different ways. The circuitry of the tank circuit could be added to the electronics module associated with each of the transducer assemblies. Alternatively, the sensors could be capacitive sensors having an integral tank circuitry. Finally, the conventional tank circuit described above (variable capacitance or variable inductance) could be configured such that the variable capacitor and one half of the inductor are fabricated on the same sensing diaphragm. The other half of the inductor is combined with a fixed electrode of the capacitor such that when the sensing diaphragm moves, the capacitance and the inductance increase or decrease together.

From the above description of the invention, those skilled in the art will perceive improvements, changes and modifications. For example, it should also be understood that the apparatuses disclosed above could be modified to monitor other conditions, such as temperature or strain, in various areas of a body. Such improvements, changes and modifications within the skill of the art are intended to be covered by the appended claims.

Having described the invention, we claim:

1. An apparatus for monitoring a condition in a body cavity, said apparatus comprising:
    at least one sensor for insertion into a body cavity, said at least one sensor for generating a signal in response to a condition inside the body cavity and said at least one sensor including at least one base member; and
    at least one telemetric device operatively coupled with said at least one sensor, said at least one telemetric device being operable to receive said signal from said at least one sensor and to transmit an EMF signal dependent upon said signal;
    said at least one telemetric device including at least one coil member extending from said at least one telemetric devices said at least one coil member each having a proximal end physically coupled to said at least one base member and a distal end for engaging a wall of the body cavity to secure said at least one base member within the body cavity, said at least one base member being spaced from the wall of the body cavity by said at least one coil member.

2. The apparatus of claim 1 further comprising a compliant enclosure surrounding said at least one sensor and a portion of said at least one telemetric device, said at least one coil member extending through the compliant enclosure.

3. The apparatus of claim 1 further comprising a film of biomolecules surrounding said at least one sensor and said at least one telemetric device.

4. The apparatus of claim 1 further comprising monolayers of biomolecules surrounding said at least one sensor and said at least one telemetric device.

5. The apparatus of claim 1 further comprising thin layers of biocompatible materials surrounding said at least one sensor and said at least one telemetric device.

6. The apparatus of claim 1 further comprising a plurality of sensors and a corresponding plurality of telemetric devices that together form a sensor network.

7. The apparatus of claim 6 wherein each of said plurality of sensors operates within a specific and distinct resonant frequency band so that said sensor network utilizes a plurality of identifiable resonant frequencies.

8. The apparatus of claim 1 wherein said at least one sensor comprises a pressure sensor.

9. The apparatus of claim 1 wherein said at least one coil member comprises a plurality of coils extending in different directions, each of said plurality of coils being engageable with the body cavity to secure said at least one base member in the body cavity.

10. The apparatus of claim 1 wherein said at least one coil member is operatively coupled with said at least one telemetric device and functions as an antenna for transmitting said EMF signal.

11. An apparatus for monitoring pressure inside an aneurysm sac, said apparatus comprising:
    at least one pressure sensor for insertion into an aneurysm sac, said at least one pressure sensor for generating an output signal in response to and indicative of the pressure inside the aneurysm sac and said at least one pressure sensor including at least one base member; and at least one telemetric device operatively coupled with said at least one pressure sensor, said at least one telemetric device being operable to receive said output signal from said at least one pressure sensor and to transmit an EMF signal dependent upon said output signal;

said at least one telemetric device including at least one coil member extending from said at least one telemetric device, said at least one coil member, each having a proximal end physically connected to said at least one base member and a distal end for engaging a wall of the aneurysm sac to secure said at least one base member within the aneurysm sac, said at least one base member being spaced from the wall of the body cavity by said at least one coil member.

12. The apparatus of claim 11 further comprising a compliant enclosure surrounding said at least one sensor and a portion of said at least one telemetric device, said compliant enclosure operating to transmit the pressure inside the aneurysm sac to said at least one pressure sensor.

13. The apparatus of claim 12 wherein said compliant enclosure comprises a balloon filled with a liquid.

14. The apparatus of claim 12 wherein said compliant enclosure is filled with silicone.

15. The apparatus of claim 12 wherein said compliant enclosure is filled with saline.

16. The apparatus of claim 12 wherein said compliant enclosure comprises a gel.

17. The apparatus of claim 12 wherein said compliant enclosure comprises gelatin.

18. The apparatus of claim 11 further comprising a film of biomolecules surrounding said at least one sensor and said at least one telemetric device.

19. The apparatus of claim 11 further comprising monolayers of biomolecules surrounding said at least one sensor and said at least one telemetric device.

20. The apparatus of claim 19 wherein said monolayers of biomolecules are selected from the group consisting of collagen, hyaluronan, glycol, and polyurethane.

21. The apparatus of claim 11 further comprising thin layers of biocompatible materials surrounding said at least one sensor and said at least one telemetric device.

22. The apparatus of claim 21 wherein said thin layers of biocompatible materials is selected from the group consisting of parylene and PDMS.

23. The apparatus of claim 11 further comprising a plurality of pressure sensors and a corresponding plurality of telemetric devices that form a sensor network.

24. The apparatus of claim 23 wherein each of said plurality of sensors operates within a specific and distinct resonant frequency band so that said sensor network utilizes a plurality of identifiable resonant frequencies.

25. The apparatus of claim 11 wherein said at least one coil member comprises a plurality of coils.

26. The apparatus of claim 11 wherein said at least one coil member is operatively coupled with said at least one telemetric device and functions as an antenna for transmitting said EMF signal.

27. The apparatus of claim 11 wherein said at least one telemetric device includes antenna means for transmitting said EMF signal.

28. An apparatus for monitoring a condition in a body cavity, said apparatus comprising:

at least one sensor for insertion into a body cavity, said at least one sensor for generating a signal in response to a condition inside the body cavity;

at least one telemetric device operatively coupled with said at least one sensor, said at least one telemetric device being operable to receive said signal from said at least one sensor and to transmit an EMF signal dependent upon said signal; and a compliant enclosure surrounding said at least one sensor and a portion of said at least one telemetric device;

said at least one telemetric device including at least one coil member that is extendable inside the body cavity to minimize migration of said at least one telemetric device in the body cavity through increased drag.

29. The apparatus of claim 28 further comprising a film of biomolecules surrounding said at least one sensor and said at least one telemetric device.

30. The apparatus of claim 28 further comprising monolayers of biomolecules surrounding said at least one sensor and said at least one telemetric device.

31. The apparatus of claim 28 further comprising thin layers of biocompatible materials surrounding said at least one sensor and said at least one telemetric device.

32. The apparatus of claim 28 further comprising a plurality of sensors and a corresponding plurality of telemetric devices that together form a sensor network.

33. The apparatus of claim 32 wherein each of said plurality of sensors operates within a specific and distinct resonant frequency band so that said sensor network utilizes a plurality of identifiable resonant frequencies.

34. The apparatus of claim 28 wherein said at least one coil member comprises a plurality of coils extending in different directions to minimize migration of said at least one telemetric device in the body cavity.

35. The apparatus of claim 28 wherein said at least one coil member is operatively coupled with said at least one telemetric device and functions as an antenna for transmitting said EMF signal.

36. A method for monitoring a condition in an internal body cavity, said method comprising the steps of:

providing a sensor for generating an output signal in response to and indicative of a condition inside the body cavity and a telemetric device for receiving the output signal from the sensor and transmitting an EMF signal dependent upon the output signal;

encapsulating the sensor and the telemetric device in a compliant enclosure to form a transducer assembly;

connecting at least one coil member with the transducer assembly, the at least one coil member projecting from the compliant enclosure;

inserting the transducer assembly into a body cavity;

attaching the transducer assembly to a wall of the body cavity with the at least one coil member, such that said at least one coil member engages with a wall of the body cavity and said transducer assembly is spaced from the wall; and monitoring the EMF signal from the sensor transmitted by the telemetric device.

37. The method of claim 36 further comprising the steps of:

inserting a plurality of transducer assemblies into the body cavity to form a sensor network, each transducer assembly becoming attached to the body cavity in a different location inside the body cavity; and monitoring the EMF signals from each of the transducer assemblies to detect variations in the condition inside the body cavity.

38. A method for monitoring a condition in an internal body cavity, said method comprising the steps of:
  providing a sensor for generating an output signal in response to and indicative of a condition inside the body cavity and a telemetric device for receiving the output signal from the sensor and transmitting an EMF signal dependent upon the output signal;
  encapsulating the sensor and the telemetric device in a compliant enclosure to form a transducer assembly;
  connecting at least one coil member with the transducer assembly, the at least one coil member being extendable from the compliant enclosure inside a body cavity;
  inserting the transducer assembly into a body cavity;
  extending the at least one coil member inside the body cavity to minimize migration of the transducer assembly in the body cavity; and
  monitoring the EMF signal from the sensor transmitted by the telemetric device.

39. The method of claim 38 further comprising the steps of:
  inserting a plurality of transducer assemblies into the body cavity to form a sensor network, the plurality of transducer assemblies being spaced apart in different locations inside the body cavity by the extended at least one coil member associated with each transducer assembly; and
  monitoring the EMF signals from each of the transducer assemblies to detect variations in the condition inside the body cavity.

* * * * *

UNITED STATES PATENT AND TRADEMARK OFFICE
CERTIFICATE OF CORRECTION

PATENT NO. : 6,682,490 B2
DATED : January 27, 2004
INVENTOR(S) : Shuvo Roy, Kenneth Ouriel and Aaron Fleischman It is certified that error appears in the above-identified patent and that said Letters Patent is hereby corrected as shown below:

Column 13,
Line 14, after "physically" change "connected" to -- coupled --

Signed and Sealed this

Twenty-seventh Day of July, 2004

JON W. DUDAS
*Acting Director of the United States Patent and Trademark Office*